United States Patent [19]
Kert

[11] Patent Number: 5,882,196
[45] Date of Patent: Mar. 16, 1999

[54] ENDODONTIC DEVICE AND METHOD FOR APPLYING FILLER MATERIAL TO ROOT CANALS

[76] Inventor: Jimmie Kert, Norrevaenget 76, DK-3500 Vaerlose, Denmark

[21] Appl. No.: 962,172

[22] Filed: Oct. 31, 1997

[51] Int. Cl.$^6$ .................................................... A61G 5/02
[52] U.S. Cl. ............................................. 433/81; 433/224
[58] Field of Search ........................................ 433/224, 81

[56] References Cited

U.S. PATENT DOCUMENTS

| | | | |
|---|---|---|---|
| 4,457,710 | 7/1984 | McSpadden | 433/81 |
| 4,758,156 | 7/1988 | Johnson et al. | 433/81 |
| 4,894,011 | 1/1990 | Johnson et al. | 433/81 |
| 5,118,297 | 6/1992 | Johnson et al. | 433/224 |
| 5,588,835 | 12/1996 | Kert et al. | 433/81 |

FOREIGN PATENT DOCUMENTS

| | | | |
|---|---|---|---|
| 194359 | 12/1933 | Switzerland | 433/224 |

*Primary Examiner*—John J. Wilson
*Attorney, Agent, or Firm*—Larson & Taylor

[57] ABSTRACT

A dental device and method are provided for applying gutta percha to a root canal of a tooth. The device includes an elongate filler member made of a biocompatible material capable of being cut so that the length of the filler member can be reduced to a desired length by a user of the device, in accordance with the length of the root canal, prior to insertion of the device into the root canal. A head portion of the filler member is of uniform thickness throughout the length thereof, and a distal end portion is uniformly tapered along the length thereof in a direction away from the head portion such that the filler member is without any discrete area of weakness throughout the length thereof. An outer sheath of thermoplastic gutta percha surrounding a portion of the distal end of the filler member. An indicator at the proximal end of the filler member assists the user in determining the portion thereof to be cut off to achieve the desired length.

14 Claims, 1 Drawing Sheet

ENDODONTIC DEVICE AND METHOD FOR APPLYING FILLER MATERIAL TO ROOT CANALS

FIELD OF THE INVENTION

The present invention relates to dental devices or tools used in filling an endodontically prepared root canal or the like, and to methods for applying the filler material.

BACKGROUND OF THE INVENTION

In U.S. Pat. Nos. 4,758,156 to Johnson, 4,894,011 to Johnson, and 5,118,297 to Johnson, there are described devices or tools for applying filler material, such as gutta percha or the like, to an endodontically prepared root canal of a tooth of a patient. The devices disclosed in these patents generally comprise a filler member or body, also referred to as obturator, in the form of an elongated shaft having a proximal handle portion. The proximal and distal portions of the obturator are severed or broken apart after the obturator is placed into the root canal so as to leave the distal portion in the canal.

In the first two patents mentioned above, the severing or breaking of the body portion of the obturator is made manually at a preformed, weakened point in the body. This approach is not practical because of the very high risk of prematurely breaking the obturator at the weakened point when inserting the obturator into a curved root canal. Further, because the weakened point is predetermined, the dentist has no discretion in choosing the length of the remaining distal portion of the obturator.

In the third patent mentioned above, U.S. Pat. No. 5,118,297, severing of the body must be carried out by use of either a heating instrument or a burr, and this also has drawbacks given the limited space in the root canal and pulpal chamber in which the dentist has to work.

A further device of this type is disclosed in U.S. Pat. No. 5,588,835 to Kert. This device includes a central filler body which surrounds an insulation rod, and the latter is withdrawn after insertion, leaving the filler body in the canal. However, the filler body in the canal still must be trimmed after withdrawal of the central insertion rod.

SUMMARY OF THE INVENTION

In accordance with the present invention, a device or tool is provided which overcomes the problems of prior art devices discussed hereinbefore. The device has a core filler member which is surrounded by thermoplastic gutta percha and which is of a length that can be adjusted prior to insertion so that it is no longer necessary to sever or cut a filler body after the insertion thereof into a root canal. Preferably, the filler member has an elongated body which is of sufficient length to accommodate the majority of root canals and which is tapered to fit the majority of endodontically prepared root canals.

According to one aspect of the invention, a dental device is provided for applying gutta percha to a root canal of a tooth, the device comprising an elongate filler member made of a biocompatible material capable of being cut so that the length of said filler member can be reduced to a desired length by a user of the device in accordance with the length of the root canal prior to insertion of the device into the root canal, the filler member having a proximal head portion and a distal end portion, the head portion being of uniform thickness throughout the length thereof, and the distal end portion being uniformly tapered along the length thereof in a direction away from the head portion such that the filler member is without any discrete area of weakness throughout the length thereof, and an outer sheath of thermoplastic gutta percha surrounding at least a portion of the distal end of the filler member.

Preferably, the filler member includes indicator means at the proximal end thereof for assisting a user in determining the portion thereof to be cut off to achieve said desired length. Advantageously, the indicator means comprises a plurality of longitudinally spaced, circular grooves in the proximal end of the filler member.

In one embodiment, the proximal end is solid, and a handle device is preferably affixed to that proximal end, the handle device including a tubular shank portion in which the proximal end is received.

In another embodiment, the proximal end includes a longitudinal bore therein, and a handle device is preferably affixed to that proximal end, the handle device including a shank portion received in the bore in the proximal end.

In accordance with a further aspect of the invention, a method of filling an endodontically prepared root canal is provided, the method comprising: comparing an endodontically prepared root canal with an elongate, tapered filler member adapted for insertion into the root canal so as to determine a desired length for said filler member, said filler member being made of biocompatible material capable of being cut, having a proximal end and a distal end and being surrounded over a portion of the distal end thereof by a sheath of gutta percha; cutting off a portion of the proximal end of the filler member so that the filler member is of said desired length; softening the gutta percha; and inserting the cut filler member into the root canal.

In one embodiment, the filler member includes a longitudinal bore therein, and the inserting of the filler member comprises engaging the bore of the filler member with an instrument having a portion which is received in said bore and using the instrument to insert the filler member into the root canal. As noted above, the instrument preferably comprises a handle device including a handle and a solid shank, extending outwardly from the handle, of a size permitting receipt thereof in the bore.

In another embodiment, the filler member is of a solid construction, and inserting of the filler member comprises using an instrument to engage an outside surface portion of the proximal end of the filler member and employing the instrument to insert the filler member into the root canal. As above, in this embodiment, the instrument preferably comprises a handle device including a handle and a tubular shank extending outwardly from the handle.

Other features and advantages of the invention will be set forth in, or apparent from, the detailed description of preferred embodiments thereof found below.

DESCRIPTION OF THE PREFERRED EMBODIMENTS

Figure 1:
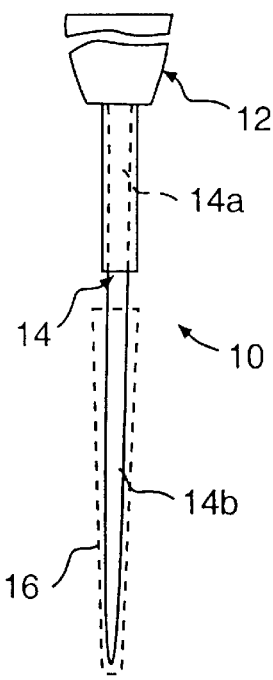
FIG. 1 is a front elevational view of a first embodiment of the device or tool of the present invention, shown in combination with an advantageous handle device.
Figure 3:
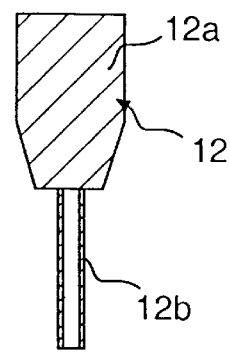
FIG. 3 is a cross-sectional view of the handle device also shown in FIG. 1 and suitable for use with the embodiments of FIGS. 1 and 2.

Referring to FIG. 1, there is shown a first embodiment of the tool or device of the invention, which is generally denoted as 10, in combination with a special handle 12, shown in more detail in FIG. 3. Although handle 12 provides advantages, it is to be understood that tool 10 can be inserted in ways other than by using handle 12, i.e., another instrument such as a pair of tweezers can be used for this purpose. In the embodiment of FIG. 1, device 10 comprises a tapered, elongate filler member 14 of solid construction made of a biocompatible material such as a thermoplastic polymer or a mixture of thermoplastic polymers. Filler member 14 includes a generally cylindrical proximal end 14a and a tapered distal end 14b, and the length thereof is sufficient to accommodate the majority of root canals. Further, the tapering of distal end 14b is such as to be accommodated in, i.e., to fit into, the majority of endodontically prepared root canals.

A tapered or conically shaped thermoplastic gutta percha sheath or sleeve 16 surrounds the tapered distal portion 14b of member 14.

Figure 6:
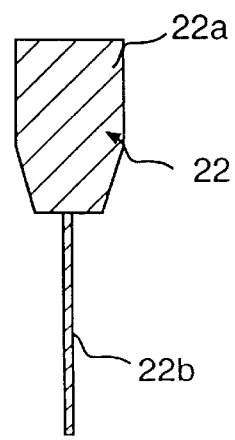
FIG. 6 is a cross-sectional view of a further embodiment of a handle device, suitable for use with the embodiments of FIGS. 4 and 5.

As shown in FIG. 3, handle device 12 includes a handle portion 12a for gripping by a user and a hollow or tubular shank 12b extending outwardly therefrom which, as shown in FIG. 6, fits around the proximal end 14a of a filler member 14.

Figure 2:
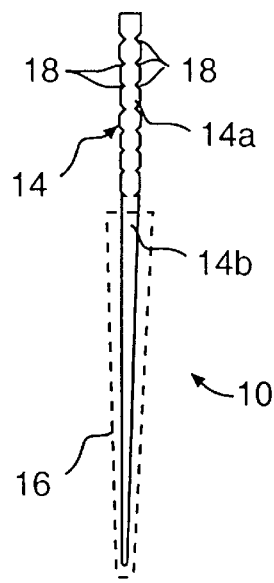
FIG. 2 is a front elevational view of an alternative embodiment of that shown in FIG. 1.

Referring to FIG. 2, a further embodiment is shown which is similar to that of FIG. 1 and differs from that of FIG. 1 in the provision therein of a plurality of longitudinally spaced grooves or impressions 18, which form a scale or indicator means. More particularly, grooves 18 provide a user with an indication of the length of the filler member 14 at various points therealong and thus assist the user in cutting off the filler member 14 at a point which produces a filler member of the designed length, based on the length of the root canal to be filled.

Figure 4:
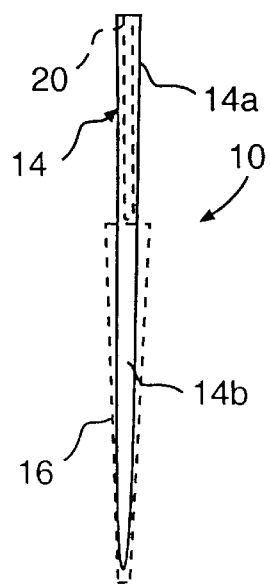
FIG. 4 is a front elevational view of a further embodiment of the invention.
Figure 5:
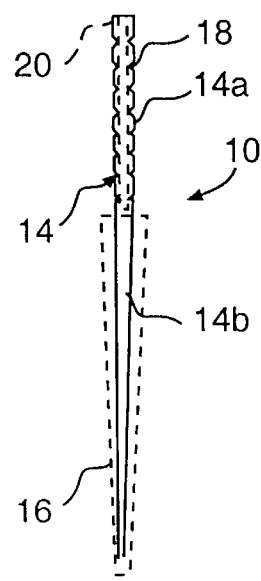
FIG. 5 is a front elevational view of an alternative embodiment of that shown in FIG. 4.

Referring to FIG. 4, a further embodiment of the invention is shown. This embodiment is similar to that of FIG. 1 but differs therefrom because of the provision of an axial or longitudinal bore 20 in the proximal end 14a of filler member 14. The embodiment of FIG. 5 is similar to that of FIG. 4 but includes grooves 18 corresponding to those of FIG. 2. The bore 20 of the embodiments of FIGS. 4 and 5 is used to permit gripping of filler member 14 by, advantageously, an instrument such as the handle device 22 shown in FIG. 6, although different instruments, such as a file or other pointed device, can also be used.

As shown in FIG. 6, the handle device 20 includes a handle portion 22a and a solid shank 22b which extends outwardly therefrom and is adapted to be inserted into bore 20.

In the method of the invention, a determination is first made by the dentist, or other user of the desired or preferred length of member 14 based on the length of the root canal being worked on. Once this determination is made, the total length of member 14 is adjusted, i.e., reduced, by cutting off the part of the proximal end 14a necessary to produce this result. In the embodiments of FIGS. 2 and 4, the scale formed by annular grooves 18 can be used to facilitate this procedure. With the filler member 14 cut to length and after softening the gutta percha 16, the filler member 14 is inserted into the root canal.

For the embodiments of FIGS. 4 and 5, wherein the proximal end 14a is hollow, i.e., includes bore 20, the dentist can use a file or a part of such a file, in inserting the device 10 into the root canal. Alternatively, and advantageously, the handle device 22 of FIG. 6 can be used for this purpose. As noted above, handle device 22 includes solid shank 22b which fits into bore 20.

Although the invention has been described in relation to exemplary preferred embodiments thereof, it will be understood by those skilled in the art that variations and modifications can be effected in these exemplary embodiments without departing from the scope and spirit of the invention.

I claim:

1. A dental device for applying gutta percha to a root canal of a tooth, said device comprising:

an elongate filler member made of a biocompatible material capable of being cut so that the length of said filler member can be reduced to a desired length by a user of the device in accordance with the length of the root canal prior to insertion of the device into the root canal, said filler member having a proximal head portion and a distal end portion, said head portion being of uniform thickness throughout the length thereof and said distal end portion being uniformly tapered along the length thereof in a direction away from said head portion such that said filler member is without any discrete area of weakness throughout the length thereof, and an outer sheath of thermoplastic gutta percha surrounding at least a portion of the distal end portion of said filler member, said proximal head portion being sold, and said device further comprising a handle affixed to said proximal head portion, said handle including a tubular shank portion in which said proximal head portion is received.

2. A device as claimed in claim 1, wherein said filler member includes indicator means at the proximal end thereof for assisting a user in determining the portion thereof to be cut off to achieve said desired length.

3. A device as claimed in claim 2, wherein said indicator means comprises a plurality of longitudinally spaced, circular grooves in the proximal end of said filler member.

4. A device for applying gutta percha to an endodontically prepared root canal of a tooth, said device comprising:

an elongate, tapered filler member made of a biocompatible material capable of being cut so that the length of said filler member can be reduced to a desired length by a user of the device in accordance with the length of the root canal prior to insertion of the device into the root canal, said filler member tapering between a proximal head portion and a distal end and including length indicator means along a portion of the proximal end thereof for assisting a user in determining the portion of the length of said filler member to be cut off to achieve said desired length, and an outer sheath of gutta percha surrounding at least a portion of the distal end of said filler member;

said proximal head portion being solid, and said device further comprising a handle affixed to said proximal head portion, said handle including a tubular shank portion in which said proximal head portion is received.

5. A device as claimed in claim 4, wherein said indicator means comprises a plurality of longitudinally spaced, circular grooves in the proximal end of said filler member.

6. A dental device for applying gutta percha to a root canal of a tooth, said device comprising:

an elongate filler member made of a biocompatible material capable of being cut so that the length of said filler member can be reduced to a desired length by a user of the device in accordance with the length of the root canal prior to insertion of the device into the root canal, said filler member having a proximal head portion and a distal end portion, said head portion being of uniform thickness throughout the length thereof, and said distal end portion being uniformly tapered along the length thereof in a direction away from said head portion such that said filler member is without any discrete area of weakness throughout the length thereof, and an outer sheath of thermoplastic gutta percha surrounding at least a portion of the distal end portion of said filler member, said proximal head portion includes a longitudinal bore therein.

7. A device as claimed in claim 6, further comprising a handle affixed to said proximal end, said handle including a shank portion received in said bore in said proximal end.

8. A device for applying gutta percha to an endodontically prepared root canal of a tooth, said device comprising:

an elongate, tapered filler member made of a biocompatible material capable of being cut so that the length of said filler member can be reduced to a desired length by a user of the device in accordance with the length of the root canal prior to insertion of the device into the root canal, said filler member tapering between a proximal head portion and a distal end and including length indicator means along a portion of the proximal end thereof for assisting a user in determining the portion of the length of said filler member to be cut off to achieve said desired length, and an outer sheath of gutta percha surrounding at least a portion of the distal end portion of said filler member;

said proximal head portion including a longitudinal bore therein.

9. A device as claimed in claim 8, further comprising a handle affixed to said proximal end of the filler member, said handle including a shank portion received in said bore in said proximal end.

10. A method of filling an endodontically prepared root canal, said method comprising:

comparing an endodontically prepared root canal with an elongate, tapered filler member adapted for insertion into the root canal so as to determine a desired length for said filler member, said filler member being made of biocompatible material capable of being cut and having a proximal end and a distal end and being surrounded over a portion of the distal end thereof by a sheath of gutta percha;

cutting off a portion of the proximal end of said filler member so that said filler member is of said desired length;

softening the gutta percha; and inserting the cut filler member into the root canal.

11. A method as claimed in claim 10, wherein said filler member includes a longitudinal bore therein and inserting of said filler member comprises engaging the bore of the filler member with an instrument having a portion which is received in said bore and using the instrument to insert the filler member into the root canal.

12. A method as claimed in claim 10, wherein said instrument comprises a handle device including a handle and a solid shank affixed to the handle and of a size permitting receipt thereof in said bore.

13. A method as claimed in claim 10, wherein said filler member is of a solid construction and said inserting of said filler member comprises using an instrument to engage an outside surface portion of the proximal end of the filler member and employing the instrument to insert the filler member into the root canal.

14. A method as claimed in claim 13, wherein said instrument comprises a handle device including a handle and a tubular shank extending outwardly from said handle.

* * * * *